Figure 1:
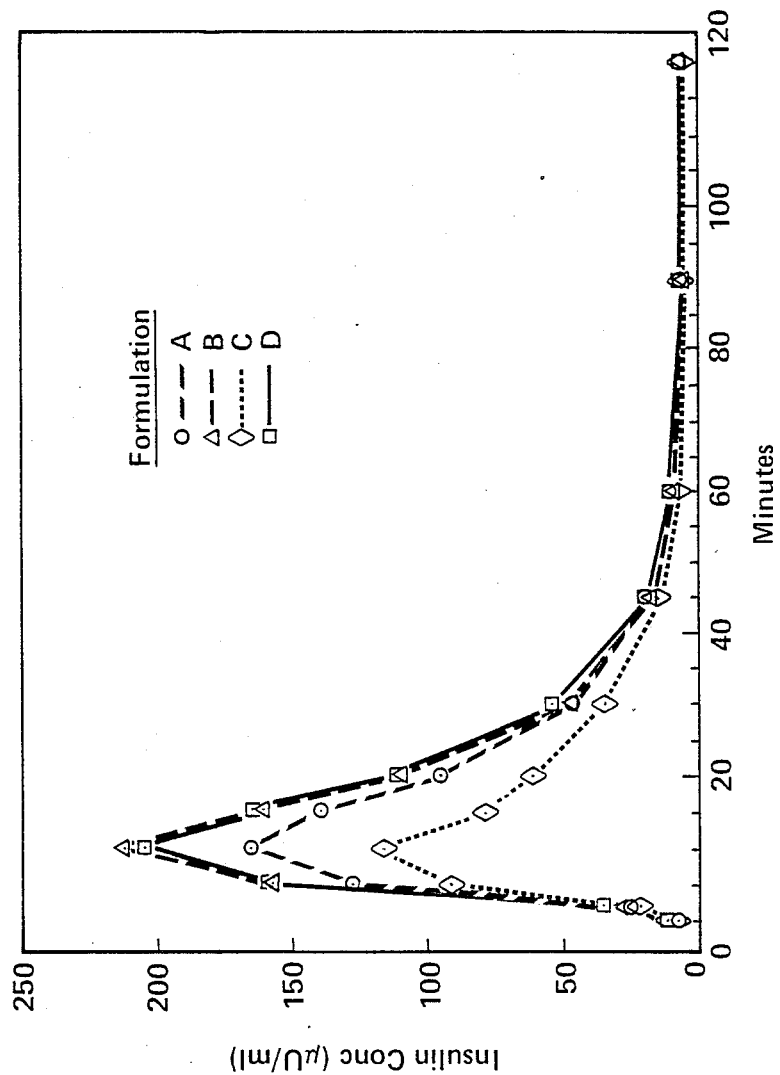

United States Patent [19]

Enever et al.

[11] Patent Number: 4,789,660

[45] Date of Patent: Dec. 6, 1988

[54] INSULIN ADMINISTRATION USING METHYL AND PROPYL PARABEN

[75] Inventors: Robin P. Enever, Rouses Point; Thomas W. Leonard, Plattsburgh; Karol K. Mikula, Morrisonville, all of N.Y.

[73] Assignee: American Home Products Corporation, New York, N.Y.

[21] Appl. No.: 95,292

[22] Filed: Sep. 10, 1987

[51] Int. Cl.$^4$ .................. C07K 7/40; A61K 37/26
[52] U.S. Cl. .................................. 514/4; 514/3; 530/303; 530/304; 530/305
[58] Field of Search ............... 530/303, 304, 305; 514/3, 4

[56] References Cited

U.S. PATENT DOCUMENTS

| | | | |
|---|---|---|---|
| 4,153,689 | 5/1979 | Hirai et al. | 514/3 |
| 4,472,385 | 9/1984 | Brange et al. | 514/3 |
| 4,476,118 | 10/1984 | Brange et al. | 514/3 |
| 4,548,922 | 10/1985 | Carey et al. | 514/4 |
| 4,608,364 | 8/1986 | Grau | 514/4 |
| 4,652,547 | 3/1987 | Chance et al. | 514/4 |
| 4,701,440 | 10/1987 | Grau | 514/3 |

FOREIGN PATENT DOCUMENTS 2104380  3/1983  United Kingdom ............ 514/3

OTHER PUBLICATIONS

Merck Index, 1976, Ninth Ed., pp. 796, 1018.

*Primary Examiner*—Howard E. Schain
*Attorney, Agent, or Firm*—Richard K. Jackson

[57] ABSTRACT

A therapeutic composition for trans-mucosal administration in the treatment of diabetes including insulin, as an adjuvant a water-soluble fusidic acid salt and as a co-adjuvant methylparaben and/or propylparaben.

9 Claims, 1 Drawing Sheet

INSULIN ADMINISTRATION USING METHYL AND PROPYL PARABEN

BACKGROUND OF THE INVENTION (a) Field of the Invention

This invention relates to a novel therapeutic composition for the treatment of diabetes, preferably by nasal administration. More particularly, this invention relates to a therapeutic composition for the treatment of diabetes which includes, in admixture, insulin and two adjuvants, the first adjuvant being an ionized or partially ionized water-soluble alkali salt of fusidic acid or a derivative thereof, and the co-adjuvant being at least one or a mixture of methylparaben and propylparaben.

(b) Prior Art

U.S. Pat. No. 4,548,922 describes a therapeutic composition for the treatment of diabetes by nasal administration which includes, in admixture, insulin and, as an adjuvant, an ionized or partially ionized water-soluble alkali salt of fusidic acid or a derivative thereof. The adjuvants described in U.S. Pat. No. 4,548,922 are useful in the present invention. In addition, British Pat. No. 1,527,605 and U.S. Pat. No. 4,153,689 have described the use of various bile salts to enhance absorption of insulin by the nasal mucosa.

SUMMARY OF THE INVENTION

According to this invention, a novel therapeutic composition for the treatment of diabetes by nasal administration is provided which includes, in admixture, insulin and two adjuvants, the first adjuvant being an ionized or partially ionized water-soluble alkali salt of fusidic acid or a derivative thereof, and the co-adjuvant being at least one or a mixture of methylparaben and propylparaben.

The ionized or partially ionized water-soluble alkali salt of fusidic acid or a derivative thereof useful in this invention are those described in U.S. Pat. No. 4,548,922 at column 2, line 20 through column 3, line 35, which U.S. Pat. No. 4,548,922 is incorporated by reference herein in its entirety.

Preferred steroids are fusidic acid; 24,25 dihydrofusidic acid, 17–20,24–25 tetrahydrofusidic acid; 3-acetoxyl-fusidic acid; cephalosporin $P_1$; and $C_{21}$ conjugates of these.

Methylparaben and propylparaben are articles of commerce and have been used extensively as preservatives in pharmaceutical preparations. The methylparaben and/or propylparaben are used in adjuvent amounts effective to increase the permeability of the mucosal surface to the drug.

The therapeutic compositions of the invention are preferably administered nasally in the form of aqueous solutions.

The following examples illustrate the formulation and the efficacy of the novel therapeutic compositions of the invention.

EXAMPLE I

A sufficient quantity of sodium tauro-24,25-dihydrofusidate was dissolved in 0.02M sodium phosphate, pH 7.4, to form a 1% final solution, weight by volume. Commercially available porcine regular insulin was then mixed in to give a final concentration of 270 U/mL. The m-cresol, benzyl alcohol and/or methylparaben and propylparaben were added to give final concentrations in the four compositions as shown below:

| Solution | |
|---|---|
| A | 270 U/mL porcine regular insulin |
|   | 1.00% w/v sodium tauro-24,25-dihydrofusidate |
|   | 0.31% w/v m-cresol |
| B | 270 U/mL porcine regular insulin |
|   | 0.99% w/v sodium tauro-24,25-dihydrofusidate |
|   | 0.14% w/v methylparaben |
|   | 0.07% w/v propylparaben |
| C | 270 U/mL porcine regular insulin |
|   | 0.99% w/v sodium tauro-24,25-dihydrofusidate |
|   | 0.76% w/v benzyl alcohol |
| D | 270 U/mL porcine regular insulin |
|   | 0.99% w/v sodium tauro-24,25-dihydrofusidate |
|   | 0.26% w/v benzyl alcohol |
|   | 0.06% w/v methylparaben |
|   | 0.03% w/v propylparaben |

Twelve normal human subjects received approximately 0.70 U/kg of insulin from each of the above formulations. This was administered intranasally with 2 equal sprays, one to each nostril. The areas under the curve for mean plasma insulin concentrations resulting from each formulation are given below.

| Solution | AUC(uU $\times$ min/mL) |
|---|---|
| A | 4233 |
| B | 4741 |
| C | 2876 |
| D | 4899 |

The formulation containing methylparaben, propylparaben and benzyl alcohol (Formulation D) resulted in a 70% increase in AUC when compared to a similar formula containing benzyl alcohol with no parabens (Formulation C) and a 16% increase in AUC when compared to that containing m-cresol (Formulation A). Formulation B, containing methylparaben and propylparaben showed a 65% increase over the one containing benzyl alcohol (Formulation C) and a 12% increase over the m-cresol containing one (Formulation A). Mean plasma levels resulting from treatment with each of the four solutions are shown in FIG. 1. The AUCs resulting from the treatments with paraben-containing formulae were statistically significantly greater than that from the other treatments ($p = 0.06$).

These results are shown in FIG. 1 of the attached drawing.

We claim:

1. A method for enhancing the permeation of insulin through the nasal mucosal membrane which comprises incorporating a nasal mucosal membrane permeability enhancing amount of a mixture of methylparaben and propylparaben in a composition containing insulin and a water soluble alkali salt of fusidic acid or a derivative thereof.

2. A method for the treatment of diabetes which comprises administering to a nasal mucosal surface of a patient in need thereof, a composition comprising,
   (a) as an active ingredient, a medically-effective amount of insulin; and
   (b) as an adjuvant, an ionized or partially ionized, water soluble alkali salt of fusidic acid or a derivative thereof, said fusidic acid or derivative being present in an amount sufficient to increase the permeation of insulin through said nasal mucosal surface; and (c) as a co-adjuvant, a mixture of methylparaben and propylparaben in an amount sufficient to further increase the permeation of insulin through said nasal mucosal surface.

3. The method of claim 2 wherein the derivative of fusidic acid is 24,25-dihydrofusidic acid.

4. The method of claim 2 wherein the derivative of fusidic acid is tauro-24,25-dihydrofusidic acid.

5. A method for insulin treatment of a diabetic patient in need of insulin therapy which comprises applying to the nasal mucosal surface of said diabetic, a composition comprising:
(a) a medically-effective amount of insulin; and
(b) as a nasal mucosal surface permeability enhancing adjuvant, an effective amount of sodium tauro-24,25-dihydrofusidic acid; and
(c) as an increased nasal mucosal surface permeability enhancing coadjuvant, an effective amount of a mixture of methylparaben and propylparaben.

6. In a medicinal formulation containing insulin and a water soluble salt of fusidic acid or a derivative thereof, for application to the nasal mucosa of a diabetic patient in need of insulin therapy, the improvement which comprises incorporating in said formulation an amount of methyl paraben and propyl paraben sufficient to increase the permeability of said nasal mucosa to insulin.

7. A medicinal composition for application to the nasal mucosa of a diabetic patient in need of insulin therapy, comprising:
(a) a medically-effective amount of insulin; and
(b) as an adjuvant, an ionized or partially ionized, water-soluble alkali salt of fusidic acid or a derivative thereof, in an amount sufficient to increase the permeation of insulin through said nasal mucosa; and
(c) as a co-adjuvant, a mixture of methylparaben and propylparaben, in an amount sufficient to further increase the permeation of insulin through said nasal mucosa.

8. The composition of claim 7 wherein the derivative of fusidic acid is 24,25-dihydrofusidic acid.

9. The composition of claim 7 wherein the derivative of fusidic acid is tauro-24,25-dihydrofusidic acid.

* * * * *